(12) United States Patent
Wu et al.

(10) Patent No.: US 10,551,310 B2
(45) Date of Patent: Feb. 4, 2020

(54) DETECTION DEVICE

(71) Applicant: Gingy Technology Inc., Hsinchu (TW)

(72) Inventors: Jen-Chieh Wu, Hsinchu (TW); Chiung-Han Wang, Hsinchu (TW); Patrick Lin, Hsinchu (TW)

(73) Assignee: Gingy Technology Inc., Hsinchu (TW)

( * ) Notice: Subject to any disclaimer, the term of this patent is extended or adjusted under 35 U.S.C. 154(b) by 62 days.

(21) Appl. No.: 16/008,057

(22) Filed: Jun. 14, 2018

(65) Prior Publication Data
US 2019/0120763 A1    Apr. 25, 2019

Related U.S. Application Data

(60) Provisional application No. 62/574,222, filed on Oct. 19, 2017, provisional application No. 62/620,985, filed on Jan. 23, 2018.

(30) Foreign Application Priority Data

Mar. 1, 2018    (CN) ...................... 2018 2 0286719 U

(51) Int. Cl.
| | | |
|---|---|---|
| *G01N 21/552* | (2014.01) | |
| *G01N 21/59* | (2006.01) | |
| *B60R 25/25* | (2013.01) | |
| *G02B 6/122* | (2006.01) | |

(52) U.S. Cl.
CPC .......... *G01N 21/554* (2013.01); *B60R 25/252* (2013.01); *G01N 2021/5903* (2013.01); *G02B 6/1226* (2013.01)

(58) Field of Classification Search
CPC . G01N 21/552–554; G01N 2021/5903; G02B 6/1226; B60R 25/252; G06K 9/0006
See application file for complete search history.

(56) References Cited

U.S. PATENT DOCUMENTS

| | | |
|---|---|---|
| 5,912,456 A | 6/1999 | Melendez et al. |
| 6,738,141 B1 | 5/2004 | Thirstrup |
| 7,221,456 B2 | 5/2007 | Kanai et al. |

(Continued)

*Primary Examiner* — Rebecca C Bryant
(74) *Attorney, Agent, or Firm* — JCIPRNET

(57) ABSTRACT

A detection device including a light guide element, a sensing element, a surface plasma resonance layer and a spatial filter element is provided. The light guide element has a top surface and a bottom surface opposite to the top surface. The sensing element is disposed beside the bottom surface of the light guide element. The surface plasma resonance layer is disposed on the top surface of the light guide element and is adapted to receive biopolymers. The spatial filter element is disposed between the bottom surface of the light guide element and the sensing element. The spatial filter element has a plurality of first light channels and a plurality of second light channels. The plurality of first light channels extend in a first direction, the plurality of second light channels extend in a second direction, and the first direction and the second direction are intersected. A normal direction of the top surface of the light guide element and the second direction form an included angle β, and the included angle β corresponds to a resonant angle γ of the surface plasma resonance layer.

11 Claims, 4 Drawing Sheets

(56) References Cited

U.S. PATENT DOCUMENTS

| | | | | |
|---|---|---|---|---|
| 7,969,422 B2* | 6/2011 | Gruhlke | ............. | G06F 3/03547 |
| | | | | 345/173 |
| 10,049,256 B2* | 8/2018 | Wu | ............. | G06K 9/0004 |
| 10,122,899 B2* | 11/2018 | Chung | ............. | H04N 5/2252 |
| 10,177,194 B2* | 1/2019 | Lin | ............. | G06K 9/00013 |
| 10,303,919 B2* | 5/2019 | Mienko | ............. | G06F 3/0421 |

* cited by examiner

DETECTION DEVICE

CROSS-REFERENCE TO RELATED APPLICATION

This application claims the priority benefits of U.S. provisional application Ser. No. 62/574,222, filed on Oct. 19, 2017, U.S. provisional application Ser. No. 62/620,985, filed on Jan. 23, 2018, and China application serial no. 201820286719.X, filed on Mar. 1, 2018. The entirety of each of the above-mentioned patent applications is hereby incorporated by reference herein and made a part of this specification.

BACKGROUND OF THE INVENTION

Field of the Invention

The disclosure relates to an optical device, and particularly relates to a detection device.

Description of Related Art

Biometric identification is applied to detect and identify faces, irises, retinas, veins and fingerprints. Since each person has unique fingerprints, and since the fingerprints do not change due to age or physical health, fingerprint identification devices have currently become the most popular biometric devices. Based on different sensing methods, the fingerprint identification devices may be further divided into optical, capacitive, ultrasonic and thermal sensing types, etc.

In the optical fingerprint identification device, image capturing of fingerprints is performed based on the principle of total reflection. When a finger is pressed against a light transmitting element, the convex portion of the fingerprint contacts the light transmitting element, and the concave portion of the fingerprint does not contact the light transmitting element. As a result, the convex portion of the fingerprint destroys the total reflection of the light beam in the light transmitting element, so that an image capturing element obtains the dark stripes corresponding to the convex portion. At the same time, the concave portion of the fingerprint does not destroy the total reflection of the light beam in the light transmitting element, so that the image capturing element obtains the bright stripes corresponding to the concave portion. Accordingly, the light beams corresponding to the convex portion and the concave portions of the fingerprint form bright/dark stripe patterns on a light receiving surface of the image capturing element. It is then possible to identify a user's identity by using algorithm to calculate the information of the corresponding fingerprint image.

In addition, the demand for detecting various physiological and health conditions of the human body has become higher and higher, e.g., detecting blood glucose concentration in the blood, the sugar content in urine or saliva, etc. Consequently, if the function of detecting physiological states may be incorporated into the fingerprint identification device, the fingerprint identification device will have a more diverse application range. However, the challenge that currently needs to be overcome is to add the function of detecting physiological states into the current fingerprint identification device without affecting the original function of the fingerprint identification device while keeping the function of detecting physiological states operating accurately.

SUMMARY OF THE INVENTION

The invention provides a detection device with good detection quality.

A detection device of the invention includes a light guide element, a sensing element, a surface plasma resonance layer and a spatial filter element. The light guide element has a top surface and a bottom surface opposite to the top surface. The sensing element is disposed beside the bottom surface of the light guide element. The surface plasma resonance layer is disposed on the top surface of the light guide element and is adapted to receive biopolymers. The spatial filter element is disposed between the bottom surface of the light guide element and the sensing element. Herein the spatial filter element has a plurality of first light channels and a plurality of second light channels. The plurality of first light channels extend in a first direction, the plurality of second light channels extend in a second direction, and the first direction and the second direction are intersected. A normal direction of the top surface of the light guide element and the second direction form an included angle $\beta$, and the included angle $\beta$ corresponds to a resonant angle $\gamma$ of the surface plasma resonance layer.

In an embodiment of the invention, the plurality of first light channels and the plurality of second light channels are alternately arranged.

In an exemplary embodiment of the invention, the normal direction of the top surface of the light guide element and the first direction form an included angle $\alpha$.

In an exemplary embodiment of the invention, the included angle $\alpha$ and the included angle $\beta$ satisfy $\alpha<\beta$.

In an exemplary embodiment of the invention, the detection device further includes a first reflective element disposed on the bottom surface of the light guide element. Herein a light beam, after being reflected by the surface plasma resonance layer and the first reflective element, is transmitted to the sensing element.

In an exemplary embodiment of the invention, the first reflective element includes a plurality of first reflective portions arranged on the bottom surface of the light guide element at intervals.

In an exemplary embodiment of the invention, the detection device further includes a second reflective element disposed on the top surface of the light guide element and spaced apart from the surface plasma resonance layer at intervals. Herein the light beam, after being reflected by the surface plasma resonance layer, the first reflective element and the second reflective element, is transmitted to the sensing element.

In an exemplary embodiment of the invention, the light beam, after being reflected by the surface plasma resonance layer, is transmitted to the first reflective element.

In an exemplary embodiment of the invention, the spatial filter element further has a plurality of third light channels and a plurality of fourth light channels. The plurality of third light channels extend in a third direction, the plurality of fourth light channels extend in a fourth direction, and the third direction and the fourth direction are intersected. The normal direction of the top surface of the light guide element and the third direction form an included angle $\beta 2$, the normal direction of the top surface of the light guide element and the fourth direction form an included angle $\beta 3$, and the included angle $\beta 2$ and the included angle $\beta 3$ satisfy $\alpha<\beta 2$, $\beta 3<\beta$.

In an exemplary embodiment of the invention, the first light channel, the second light channel, the third light channel and the fourth light channel are sequentially arranged on the sensing element.

In an exemplary embodiment of the invention, the included angle $\beta 2$ and the included angle $\beta 3$ satisfy $\alpha < \beta 2 < \beta 3 < \beta$.

Based on the foregoing, the detection device according to an embodiment of the invention includes the light guide element, the sensing element, the surface plasma resonance layer and the spatial filter element. The spatial filter element is provided with the plurality of first light channels and the plurality of second light channels. Herein the first light channels extend in the first direction, the second light channels extend in the second direction, and the first direction and the second direction are intersected. The second direction and the normal direction of the top surface of the light guide element form the included angle $\beta$, and the included angle $\beta$ corresponds to the resonant angle of the surface plasma resonance layer. The plurality of first light channels are adapted to pass the light beam reflected by the biometric feature, so that an image of the biometric feature is obtained by the sensing element. The plurality of second light channels are adapted to pass the light beam reflected by the surface plasma resonance layer so as to determine whether the type of the biopolymers to be detected is present on the surface plasma resonance layer. The detection device according to an embodiment of the invention has multiple functions of biometric identification and biological detection.

To make the aforementioned and other features and advantages of the invention more comprehensible, several embodiments accompanied with drawings are described in detail as follows.

DESCRIPTION OF THE EMBODIMENTS

Figure 1:
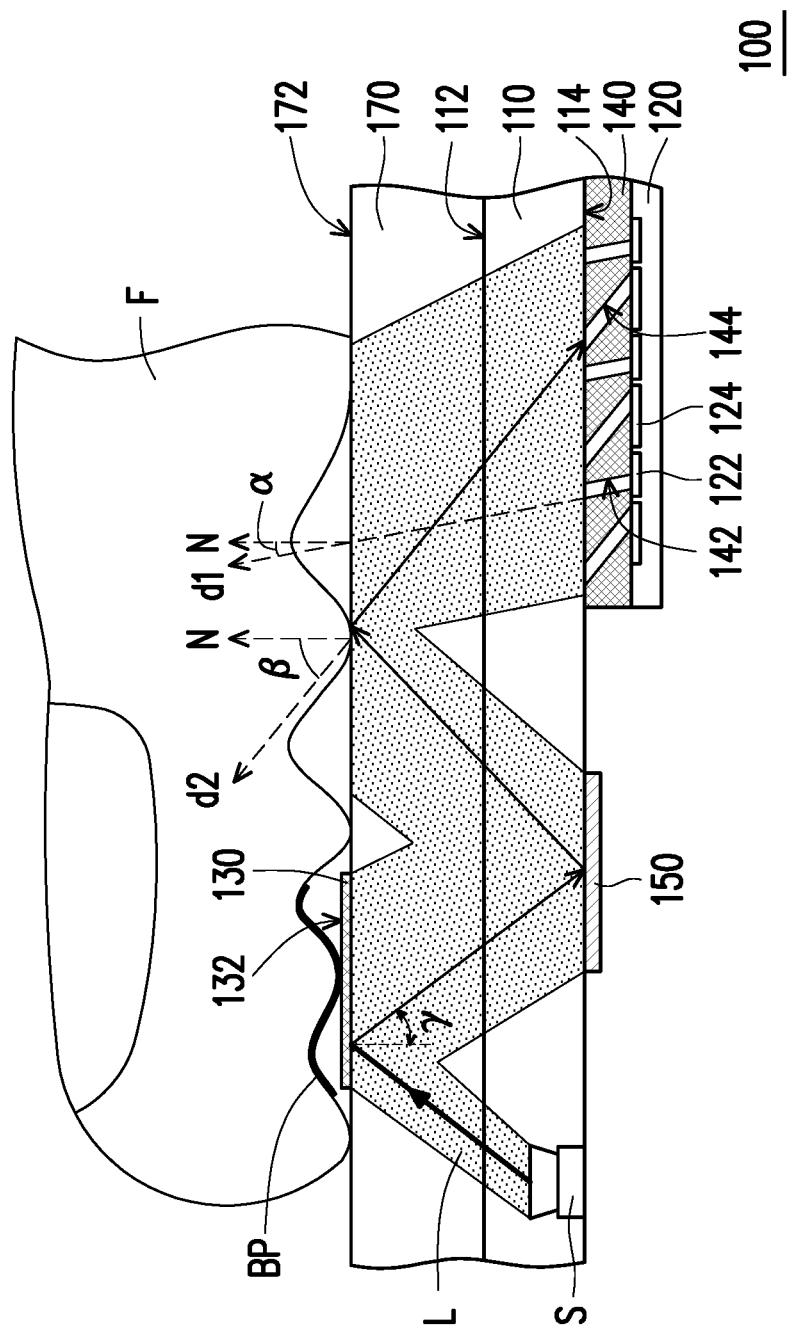
FIG. 1 is a schematic cross-sectional view of a detection device according to an embodiment of the invention.

FIG. 1 is a schematic cross-sectional view of a detection device according to an embodiment of the invention. With reference to FIG. 1, a detection device 100 includes a light guide element 110, a sensing element 120, a surface plasma resonance layer 130 and a spatial filter element 140. The light guide element 110 has a top surface 112 and a bottom surface 114 opposite to the top surface 112. In this embodiment, the light guide element 110 is an optical adhesive layer, for example. However, the invention is not limited thereto. In another embodiment, the light guide element 110 may also be a light transmitting substrate, and a material thereof may be selected from glass, polymethylmethacrylate (PMMA), polycarbonate (PC), or other suitable light transmitting materials. In this embodiment, the detection device 100 may include a light source S for emitting a light beam L. In this embodiment, the light source S may be embedded in the light guide element 110 (e.g., an optical adhesive layer). However, the invention is not limited thereto. In another embodiment, the light source S may also be disposed outside the light guide element 110. In this embodiment, the light source S may be a light-emitting diode (LED). However, the invention is not limited thereto. In other embodiments, the light source S may also be another suitable type of light emitting device.

The sensing element 120 is disposed beside the bottom surface 114 of the light guide element 110. For example, in this exemplary embodiment, the sensing element 120 is a charge coupled device (CCD) or a complementary metal-oxide semiconductor (CMOS), for example. However, the invention is not limited thereto. In other exemplary embodiments, the sensing element 120 may also be another suitable type of image sensor.

The surface plasma resonance layer 130 is disposed on the top surface 112 of the light guide element 110 and is adapted to receive biopolymers BP. In this embodiment, the detection device 100 may also selectively include a cover plate 170 located above the top surface 112 of the light guide element 110 and having a pressing surface 172 that may be pressed by a finger F. In this embodiment, the surface plasma resonance layer 130 may also be disposed on the pressing surface 172 of the cover plate 170. However, the invention is not limited thereto. In other embodiments, the cover plate 170 may also be omitted, and the surface plasma resonance layer 130 may be directly disposed on the top surface 112 of the light guide element 110.

Figure 2:
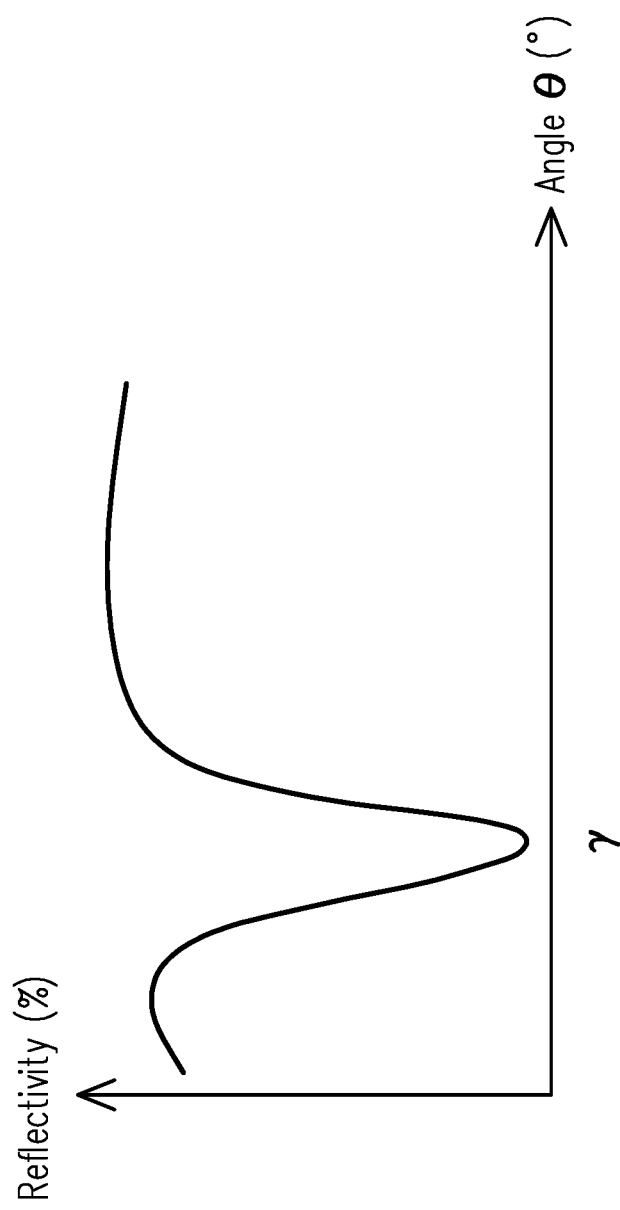
FIG. 2 shows the relationship between an incident angle $\theta$ (which may also be viewed as a reflection angle) of the light beam L incident on the surface plasma resonance layer 130 and its reflectivity.

In this embodiment, the biopolymers BP may be sweat, saliva, blood, urine, bacteria, viruses, or other biopolymers to be tested. FIG. 2 shows the relationship between an incident angle $\theta$ (which may also be viewed as a reflection angle) of the light beam L incident on the surface plasma resonance layer 130 and its reflectivity. With reference to FIG. 1 and FIG. 2, when the light beam L emitted from the light source S is transmitted to the surface plasma resonance layer 130, total internal reflection (TIR) of the light beam L occurs on a surface 132 of the surface plasma resonance layer 130, and an evanescent wave is formed in an optically thinner medium (such as an environmental medium) and a surface plasma wave is formed in an optically denser medium (such as the surface plasma resonance layer 130). At this point, the encounter between the evanescent wave and the surface plasma wave results in resonance. When the resonance occurs between the evanescent wave and the surface plasma wave, most of the energy of the light beam L incident on the surface plasma resonance layer 130 is absorbed by the surface plasma wave. As a result, the intensity of the light beam L reflected by the surface plasma resonance layer 130 and has a specific reflection angle is greatly reduced, and here the specific reflection angle is referred to as a resonant angle $\gamma$. In this embodiment, the resonant angle $\gamma$ is related to the refractive index variation of the surface 132 of the surface plasma resonance layer 130, that is, the resonant angle $\gamma$ is related to the properties (such as the dielectric constant) of the biopolymers BP attached to the surface 132 of the surface plasma resonance layer 130. By analyzing the distribution of the reflected light beam L formed on the sensing element 120, it is possible to infer the resonant angle $\gamma$ so as to further infer what type of the biopolymers BP is attached to the surface 132 of the surface plasma resonance layer 130. In addition, in this embodiment, the surface 132 of the surface plasma resonance layer 130 may selectively be a surface modification layer, so that the biopolymers BP may be attached onto the surface plasma resonance layer 130 more easily, thereby improving detection sensitivity.

The spatial filter element 140 is disposed between the bottom surface 114 of the light guide element 110 and the sensing element 120. The spatial filter element 140 has a plurality of first light channels 142 and a plurality of second light channels 144 corresponding to a plurality of pixel regions 122 and a plurality of pixel regions 124 of the sensing element 120 respectively. The plurality of first light channels 142 extend in a first direction d1, the plurality of second light channels 144 extend in a second direction d2, and the first direction d1 and the second direction d2 are intersected. That is to say, a normal direction N of the top surface 112 of the light guide element 110 and an extending direction (i.e., the first direction d1) of the first light channels 142 form an included angle α, the normal direction N of the top surface 112 of the light guide element 110 and an extending direction (i.e., the second direction d2) of the second light channels 144 form an included angle β, and the included angle α is not equal to the included angle β.

It should be noted that the included angle β corresponds to the resonant angle γ of the surface plasma resonance layer 130. In other words, the second light channel 144 has an appropriate tilt angle (i.e., the included angle β), so that a portion of the reflected light beam L having the resonant angle γ is easily transmitted to the pixel region 124 corresponding to the second light channel 144 through the second light channel 144. In this embodiment, by detecting the variation of the intensity difference between the portion of the reflected light beam L transmitted to the pixel region 124 corresponding to the second light channel 144 and a portion of the reflected light beam L transmitted to the pixel region 122 corresponding to the first light channel 142, it is possible to know whether the biopolymers BP to be detected are present on the surface 132 of the surface plasma resonance layer 130. For example, if the intensity of the portion of the reflected light beam L transmitted to the pixel region 124 corresponding to the second light channel 144 becomes lower, and if the intensity difference between the portion of the reflected light beam L transmitted to the pixel region 122 corresponding to the first light channel 142 and the portion of the reflected light beam L transmitted to the pixel region 124 corresponding to the second light channel 144 becomes greater, it is then known that the type of the biopolymers BP to be detected is present on the surface 132 of the surface plasma resonance layer 130. In short, since the tilt angle (i.e., the included angle β) of the second light channel 144 of the spatial filter element 140 corresponds to the resonant angle γ of the surface plasma resonance layer 130, the detection device 100 may easily detect whether the type of the biopolymers BP to be detected is present on the surface 132 of the surface plasma resonance layer 130.

In this exemplary embodiment, the plurality of first light channels 142 and the plurality of second light channels 144 may be alternately arranged on the sensing element 120. The plurality of first light channels 142 and the plurality of second light channels 144 are separated from each other without communicating with each other. However, the invention is not limited thereto. In other embodiments, the first light channels 142 and the second light channels 144 may also communicate with each other.

In this embodiment, the range of the included angle α may be between 0° and 90°, that is, the extending direction (i.e., the first direction d1) of the first light channels 142 may not be parallel to the normal direction N of the top surface 112. However, the invention is not limited thereto. In other embodiments, the extending direction (i.e., the first direction d1) of the first light channels 142 may also be parallel to the normal direction N of the top surface 112. In this embodiment, the range of the included angle β may be between 0° and 90°, that is, the extending direction (i.e., the second direction d2) of the second light channels 144 may not be parallel to the normal direction N of the top surface 112. For example, in this embodiment, the included angles α and β may satisfy α<β. However, the invention is not limited thereto. Since the first light channels 142 are adapted to pass the portion of the light beam that is reflected by a biometric feature (e.g., a fingerprint), the included angle α may be determined according to the range of the reflection angle of most of the light beam L reflected by the biometric feature (e.g., a fingerprint). Since the second light channels 144 are adapted to pass a partial light beam K that is reflected by the surface plasma resonance layer 130 and has the resonant angle γ, the included angle β may be determined by the properties of the biopolymers BP to be detected and the resonant angle γ of the surface plasma resonance layer 130. The included angle β is not necessarily greater than the included angle α.

In this embodiment, the detection device 100 may further include a first reflective element 150 disposed on the bottom surface 114 of the light guide element 110. The light beam L, after being reflected by the surface plasma resonance layer 130 and the first reflective element 150, is transmitted to the sensing element 120. That is, in addition to sensing the biopolymers BP, the surface plasma resonance layer 130 may also be adapted to reflect the light beam L having an angle other than the resonant angle γ so as to increase the area where the light beam L may irradiate a biometric feature (e.g., a finger F). In this embodiment, the first reflective element 150 partially overlaps with the surface plasma resonance layer 130 in the normal direction N. However, the invention is not limited thereto.

Figure 3:
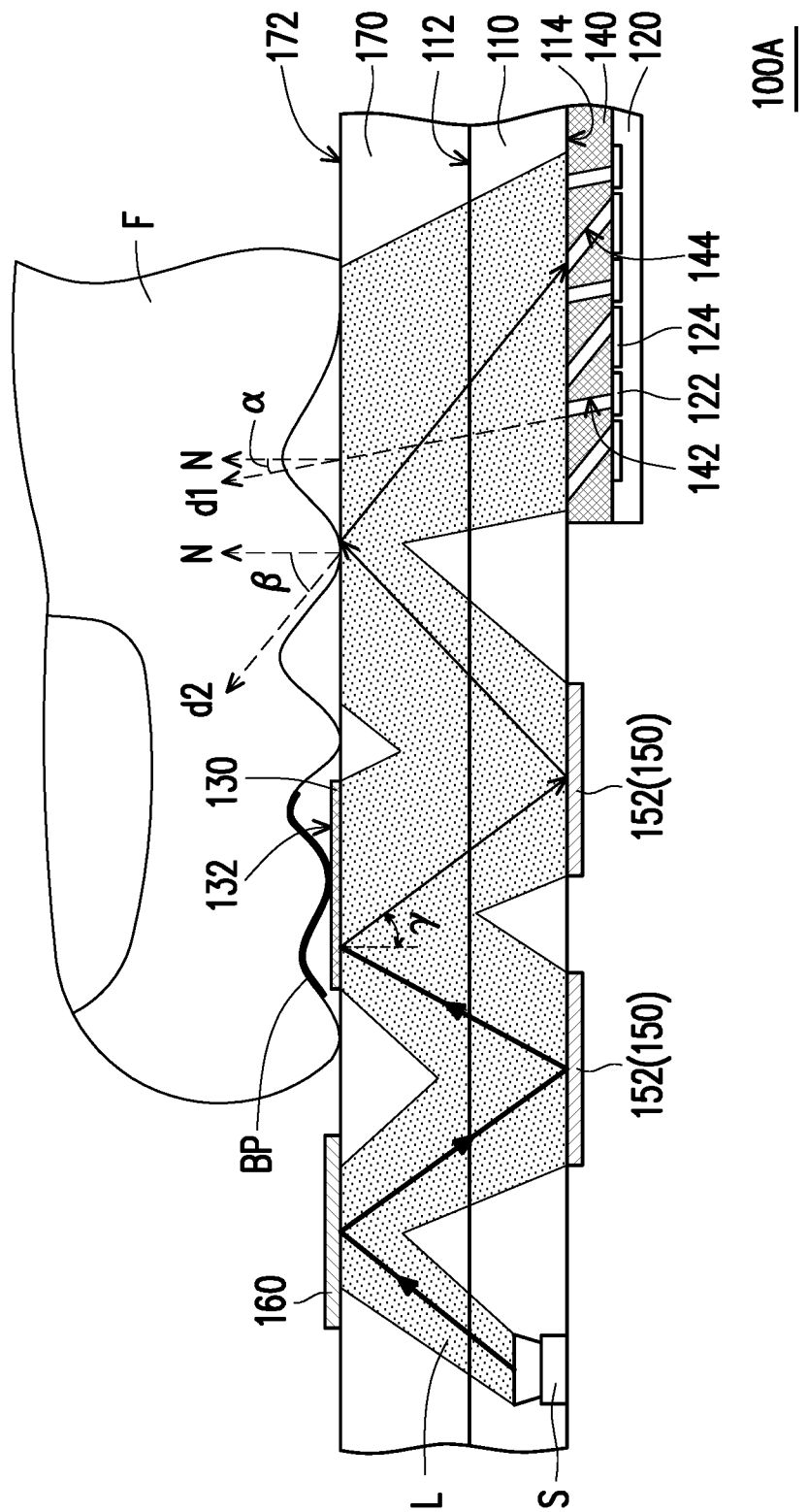
FIG. 3 is a schematic cross-sectional view of a detection device according to another embodiment of the invention.

FIG. 3 is a schematic cross-sectional view of a detection device according to another embodiment of the invention. A detection device 100A of FIG. 3 is similar to the detection device 100 of FIG. 1, and descriptions of the same technical features are not repeated hereinafter. The differences therebetween lie in that the first reflective element 150 includes a plurality of first reflective portions 152 arranged on the bottom surface 114 of the light guide element 110 at intervals, and that the detection device 100A further includes a second reflective element 160 disposed on the top surface 112 of the light guide element 110 and spaced apart from the surface plasma resonance layer 130 at intervals. The light beam L, after being reflected by the surface plasma resonance layer 130, the first reflective element 150 and the second reflective element 160, is transmitted to the sensing element 120. In the embodiment of FIG. 3, the second reflective element 160 consists of a single reflective pattern. However, the invention is not limited thereto. In other embodiments, the second reflective element 160 may also include a plurality of second reflective portions (not shown) arranged on the top surface 112 of the light guide element 110 at intervals.

Figure 4:
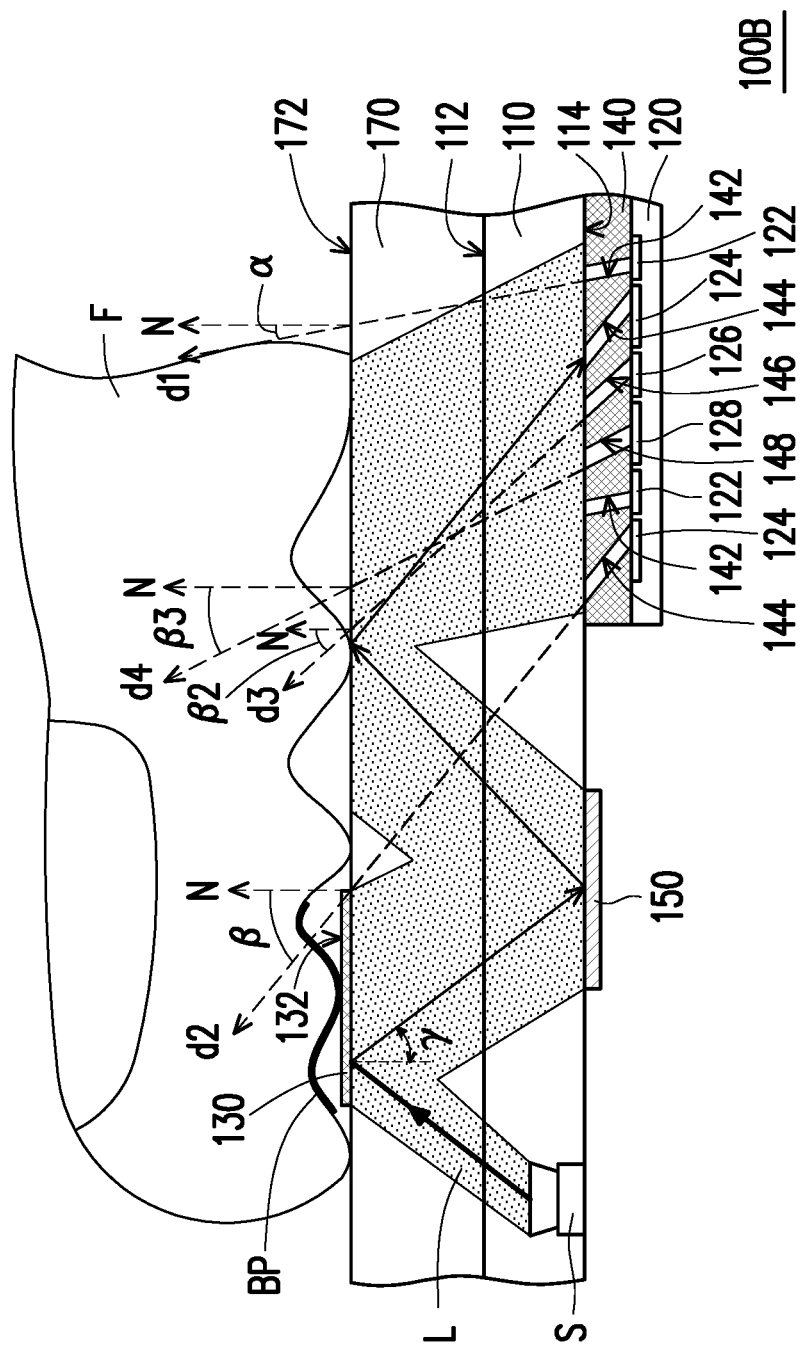
FIG. 4 is a schematic cross-sectional view of a detection device according to yet another embodiment of the invention.

FIG. 4 is a schematic cross-sectional view of a detection device according to yet another embodiment of the invention. A detection device 100B of FIG. 4 is similar to the detection device 100 of FIG. 1, and descriptions of the same technical features are not repeated hereinafter. The differences therebetween lie in that the spatial filter element 140 further has a plurality of third light channels 146 and a plurality of fourth light channels 148 corresponding to a plurality of pixel regions 126 and a plurality of pixel regions 128 of the sensing element 120 respectively. The plurality of third light channels 146 extend in a third direction d3, the plurality of fourth light channels 148 extend in a fourth direction d4, and the third direction d3 and the fourth direction d4 are intersected. That is to say, the normal direction N of the top surface 112 of the light guide element 110 and an extending direction (i.e., the third direction d3) of the third light channels 146 form an included angle β2, the normal direction N of the top surface 112 of the light guide element 110 and an extending direction (i.e., the fourth direction d4) of the fourth light channels 148 form an included angle β3, and the included angle β2 is not equal to the included angle β3. In this exemplary embodiment, the first light channel 142, the second light channel 144, the third light channel 146 and the fourth light channel 148 are sequentially arranged on the sensing element. However, the invention is not limited thereto. In other embodiments, the arrangement sequence of the first light channel 142, the second light channel 144, the third light channel 146 and the fourth light channel 148 may also be adjusted according to actual conditions. In this embodiment, the included angles β2 and β3 may be located between the included angle α and the included angle β, i.e., satisfying α<β2, β3<β, and the degrees of the included angles α, β, β2 and β3 may be gradually increased, i.e., satisfying α<B2<β3<β. However, the invention is not limited thereto. In this embodiment, the spatial filter element 140, besides having the plurality of first light channels 142, the plurality of second light channels 144, the plurality of third light channels 146 and the plurality of fourth light channels 148, may also have a plurality of light channels with angles different from the included angles α, β, β2 and β3, such as having a fifth light channel (not shown) and a sixth light channel (not shown) with different included angles. Herein the number of light channel with different included angles may be increased adaptively.

It should be noted that since the resonant angle γ of the surface plasma resonance layer 130 changes due to different types of the biopolymers BP, the plurality of light channels having the different included angles α, β, β2 and β3 are provided in the spatial filter element 140 and may respectively correspond to the resonant angles γ generated by the multiple types of the biopolymers BP. Therefore, the detection device 100B is able to detect more than one type of the biopolymers BP, so that the application range of the detection device 100B is even more diverse.

In summary, the detection device according to an exemplary embodiment of the invention includes the light guide element, the sensing element, the surface plasma resonance layer and the spatial filter element. The spatial filter element is provided with the plurality of first light channels and the plurality of second light channels. Herein the first light channels extend in the first direction, the second light channels extend in the second direction, and the first direction and the second direction are intersected. The second direction and the normal direction of the top surface of the light guide element form the included angle β, and the included angle β corresponds to the resonant angle of the surface plasma resonance layer. The plurality of first light channels are adapted to pass the light beam reflected by the biometric feature, so that an image of the biometric feature is obtained by the sensing element. The plurality of second light channels are adapted to pass the light beam reflected by the surface plasma resonance layer so as to determine whether the type of the biopolymers to be detected is present on the surface plasma resonance layer. The detection device according to an exemplary embodiment of the invention has multiple functions of biometric identification and biological detection.

Although the embodiments are already disclosed as above, these embodiments should not be construed as limitations on the scope of the invention. It will be apparent to those skilled in the art that various modifications and variations can be made to the disclosed embodiments without departing from the scope or spirit of this invention. In view of the foregoing, it is intended that the invention covers modifications and variations provided that they fall within the scope of the following claims and their equivalents.

What is claimed is:

1. A detection device, comprising:
    a light guide element having a top surface and a bottom surface opposite to the top surface;
    a sensing element disposed beside the bottom surface of the light guide element;
    a surface plasma resonance layer disposed on the top surface of the light guide element and adapted to receive a biopolymer; and
    a spatial filter element disposed between the bottom surface of the light guide element and the sensing element, wherein the spatial filter element has a plurality of first light channels and a plurality of second light channels, the plurality of first light channels extend in a first direction, the plurality of second light channels extend in a second direction, the first direction and the second direction are intersected, a normal direction of the top surface of the light guide element and the second direction form an included angle β, and the included angle β corresponds to a resonant angle γ of the surface plasma resonance layer.

2. The detection device as recited in claim 1, wherein the plurality of first light channels and the plurality of second light channels are alternately arranged.

3. The detection device as recited in claim 1, wherein the normal direction of the top surface of the light guide element and the first direction form an included angle α.

4. The detection device as recited in claim 3, wherein the included angle α and the included angle β satisfy α<β.

5. The detection device as recited in claim 1, further comprising:
    a first reflective element disposed on the bottom surface of the light guide element, wherein a light beam, after being reflected by the surface plasma resonance layer and the first reflective element, is transmitted to the sensing element.

6. The detection device as recited in claim 5, wherein the first reflective element comprises:
    a plurality of first reflective portions arranged on the bottom surface of the light guide element at intervals.

7. The detection device as recited in claim 5, further comprising:
    a second reflective element disposed on the top surface of the light guide element and spaced apart from the surface plasma resonance layer at intervals, wherein the light beam, after being reflected by the surface plasma resonance layer, the first reflective element and the second reflective element, is transmitted to the sensing element.

8. The detection device as recited in claim 5, wherein the light beam, after being reflected by the surface plasma resonance layer, is transmitted to the first reflective element.

9. The detection device as recited in claim 1, wherein the spatial filter element further has a plurality of third light channels and a plurality of fourth light channels, the plurality of third light channels extend in a third direction, the plurality of fourth light channels extend in a fourth direction, the third direction and the fourth direction are intersected, the normal direction of the top surface of the light guide element and the third direction form an included angle β2, the normal direction of the top surface of the light guide element and the fourth direction form an included angle $\beta$, and the included angle $\beta 2$ and the included angle $\beta 3$ satisfy $\alpha<\beta 2$, $\beta 3<\beta 3$.

10. The detection device as recited in claim 9, wherein the first light channel, the second light channel, the third light channel and the fourth light channel are sequentially arranged on the sensing element.

11. The detection device as recited in claim 10, wherein the included angle $\beta 2$ and the included angle $\beta 3$ satisfy $\alpha<\beta 2<\beta 3<\beta$.

* * * * *